United States Patent [19]

Trofimenko et al.

[11] Patent Number: 5,189,138
[45] Date of Patent: Feb. 23, 1993

[54] COMPOUNDS, MONOMERS, AND POLYMERS BASED ON PERFLUOROALKYL AND PERFLUOROALKYL-ARYL DIOXAPENTACENE

[75] Inventors: Swiatoslaw Trofimenko, Wilmington; Brian C. Auman, Newark, both of Del.

[73] Assignee: E. I. du Pont de Nemours and Company, Wilmington, Del.

[21] Appl. No.: 661,595

[22] Filed: Feb. 20, 1991

[51] Int. Cl.$^5$ .................... C08G 63/00; C08G 73/10; C07D 311/78; C07D 307/77
[52] U.S. Cl. .................... 528/183; 528/125; 528/170; 528/172; 528/173; 528/176; 528/185; 528/188; 528/190; 528/191; 528/329.1; 528/350; 528/353; 549/234; 549/382
[58] Field of Search .............. 528/125, 350, 176, 353, 528/183, 329.1, 185, 170, 188, 190, 191, 172, 173; 549/382, 234

[56] References Cited

U.S. PATENT DOCUMENTS 5,051,520  9/1991  Trofimenko .................... 528/185
5,097,000  3/1992  Trofimenko .................... 528/353
5,101,006  3/1992  Stults .......................... 528/353

FOREIGN PATENT DOCUMENTS 0398205  5/1990  European Pat. Off.
0458201  5/1991  European Pat. Off.

Primary Examiner—John Kight, III
Assistant Examiner—P. Hampton-Hightower

[57] ABSTRACT

Rigid fluorine-containing compounds, monomers, and polymers based on pentacyclic core systems, such as 12H,14H-5, 7-dioxapentacene with perfluoroalkyl and/or aryl groups in the 12, 14 positions, and 5H,12H-7, 14-dioxapentacene, with perfluoroalkyl and/or aryl groups in the 5,12 positions. These monomers have utility in the preparation of advanced high-performance polymers, particularly polyimides. The rigid pentacyclic core decreases the coefficient of thermal expansion of the polymers, while the fluorinated substituents improve the dielectric constant and water absorption properties. Each monomer unit contains within its pentacyclic core two-O-bridges, and two —CRR$_f$ bridges (where R is aryl, substituted aryl or perfluoroalkyl, and R$_f$ is perfluoroalkyl).

24 Claims, No Drawings

COMPOUNDS, MONOMERS, AND POLYMERS BASED ON PERFLUOROALKYL AND PERFLUOROALKYL-ARYL DIOXAPENTACENE

FIELD OF THE INVENTION

The present invention pertains to fluorinated polycyclic dioxapentacene compounds, monomers, and polymers prepared therefrom.

BACKGROUND OF THE INVENTION

The ever more stringent performance requirements of the electronic packaging industry mandate the development of polymers with lower dielectric constant and lower moisture absorption. Improvement in these properties has in the past been effected by the introduction of fluorine into the polymer. Unfortunately, this was always accompanied by deterioration of other properties, such as lowering of the glass transition temperature, increasing the coefficient of thermal expansion, and increasing solvent sensitivity. Accordingly, the present invention relates to a new class of stiff, fluorinated monomers, based on two novel pentacyclic core systems, 12H,14H-5,7-dioxapentacene containing perfluoroalkyl, or perfluoroalkyl and aryl substituents in the 12,14 positions, and on 5H,12H,7-14-dioxapentacene containing perfluoroalkyl, or perfluoroalkyl and aryl substituents in the 5,12 positions.

These monomers have utility in the preparation of advanced high-performance polymers, particularly polyimides. The rigid pentacyclic core decreases the coefficient of thermal expansion of the polymers, while the fluorinated substituents improve the dielectric constant, and water absorption properties.

SUMMARY OF THE INVENTION

According to the present invention there is provided a composition of matter comprising at least one of the isomeric structures having the formula

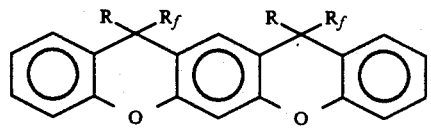

or

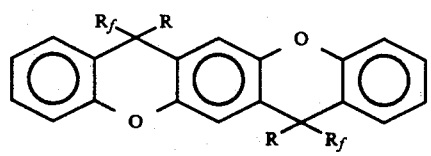

wherein R is selected from the group consisting of aryl, substituted aryl, and perfluoroalkyl; and $R_f$ is perfluoroalkyl.

There is also provided a composition of matter comprising at least one of the isomers having the formula

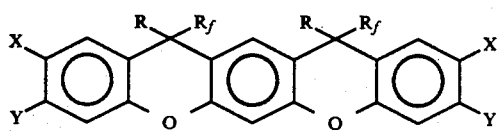

or

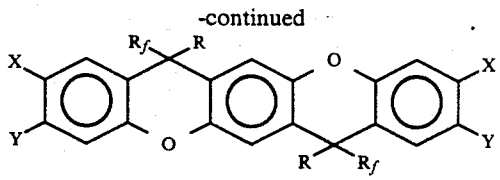

wherein R is selected from the group consisting of aryl, substituted aryl, and perfluoroalkyl; $R_f$ is perfluoroalkyl; X is selected from the group consisting of H, alkyl, COOH, COCl, $NH_2$, halogen, $SO_2$ alkyl and NCO; Y is selected from the group consisting of X and OH; and X and Y on each aromatic ring are together $-CO-O-CO-$.

In addition, there is provided a process for preparing a composition comprising at least one of the monomers having the formula

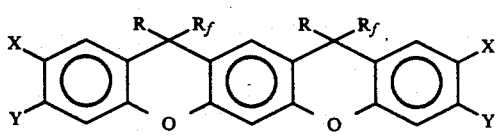

or

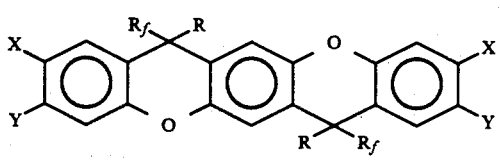

wherein R is selected from the group consisting of aryl, substituted aryl and perfluoroalkyl; $R_f$ is perfluoroalkyl; X is H or alkyl; and Y is H, alkyl, $NH_2$ or OH; comprising reacting $RCOR_f$ with a diether precursor having the formula

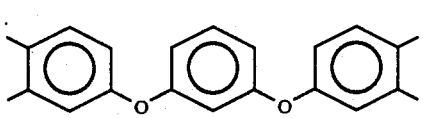

(I)

or

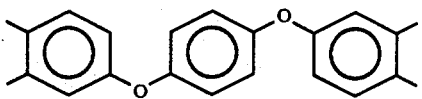

respectively, wherein R, $R_f$, X and Y are as defined above, in hydrofluoric acid solvent at a temperature of from 110° C. to 180° C.

Further, there is provided a process for preparing a dianhydride having at least one isomer of the formula

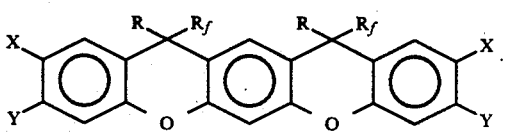

or

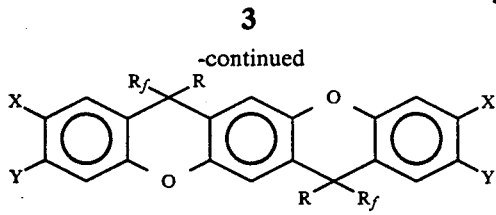

wherein R is selected from the group consisting of aryl, substituted aryl and perfluoroalkyl; $R_f$ is perfluoroalkyl; and X and Y together are —CO—O—CO— comprising (a) oxidizing a precursor having the above formula wherein both X and Y are $CH_3$ to form a tetraacid of the above formula wherein both X and Y are COOH; and (b) dehydrating the tetraacid to form the dianhydride.

Finally, there is provided a polyimide having the following recurring structural unit, including isomeric forms

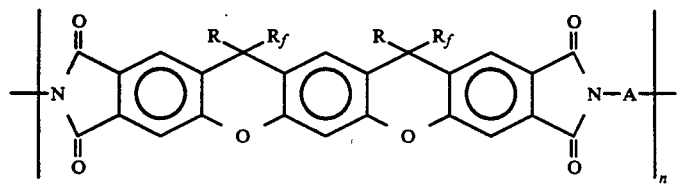

wherein R is selected from the group consisting of aryl, substituted aryl and perfluoroalkyl; $R_f$ is perfluoroalkyl; A is a divalent radical of a diamine containing at least two carbon atoms, the two amino groups of the diamine each being attached to separate carbon atoms of said divalent radical; and n is a positive integer.

In the above definitions perfluoroalkyl for R and $R_f$ will generally contain from 1 to 20 carbon atoms and preferably from 1 to 8 carbon atoms.

DETAILED DESCRIPTION OF THE INVENTION

The novel compositions of this invention contain three aryl rings linked by two-O-bridges, and by two-$CRR_f$ bridges, where $R_f$ is a perfluoroalkyl group, and R may be a perfluoroalkyl group or an aryl ring. In the case where R is different than $R_f$, cis- and trans-isomers may be present, based on the relative positions of the nonidentical R and $R_f$ substituents, with reference to the molecular plane. The main pentacyclic cores, and their numbering are exemplified below.

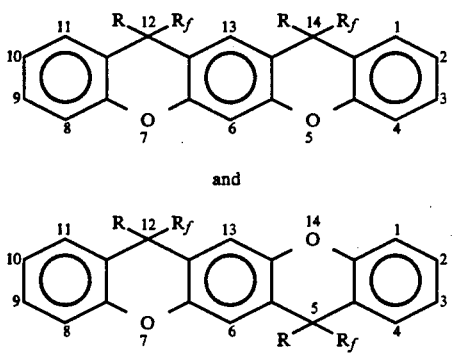

According to the present invention there are provided compositions of matter and their preparation thereof having the general formulas shown above with possible substituents especially in positions 1–11, as well as of monomers and polymers derived therefrom, as described hereinunder. Although the additional substituents may be present in any of the positions 1–11, it is preferable to maintain substituents in positions 2, 3, 9, and 10. Polymers may be made from both isomeric structures depicted above. Although in some instances only one of the two isomeric structures is shown as an example, it should be understood that the alternate isomeric structure or mixtures of the two structures may also be used.

Pentacyclic core ring systems of compositions of the instant invention may be prepared by a cyclobridging process, in which a diether precursor, such as for example 1,3-bis(3,4-dimethylphenoxy)benzene or 1,4-bis (3,4-dimethylphenoxy)benzene reacts with a bis(perfluoroalkyl) ketone or with aryl perfluoroalkyl ketone, for example. When both substituents on the bridging carbon are perfluoroalkyl groups, it is necessary that one of them be a trifluoromethyl group. There is no such limitation on $R_f$ when one of the substituents on the bridging carbon is an aryl group.

The parent heterocycles, 12,12,14,14-tetrakis(trifluoromethyl) -12H,14H-5,7-dioxapentacene and 12,14-diphenyl-12,14-bis(trifluoromethyl)-12H,14H-5,7-dioxapentacene may be prepared by decarboxylation of the 2,3,9,10-tetracarboxylic acid precursors, for example in the presence of quinoline and Copper:

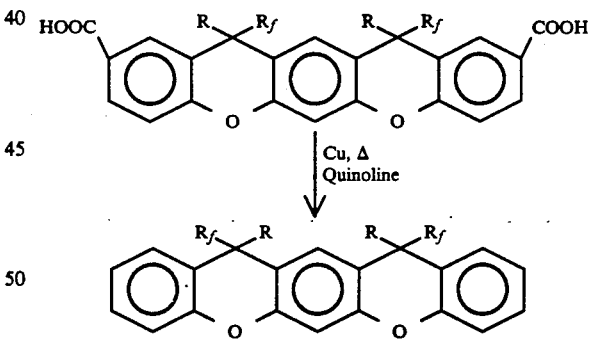

Other aromatic ethers, terminated by 4-methylphenoxy groups can also be used in the cyclobridging reaction. For instance, 1,3-bis(4-methylphenoxy) benzene will react with $RCOR_f$ compounds (R and $R_f$ defined as above) to yield 2,10-dimethyl-12,14-(R) 2-12,14-$(R_f)$2-12H,14H-5,7-dioxapentacene. The 2,10-methyl groups may be oxidized by conventional means to the dicarboxylic acids, which are useful monomers for the preparation of polymers, such as polyamides and polyesters, for example. The diacids may also be converted by treatment with, for instance, thionyl chloride to the diacyl chlorides which also are useful polymer intermediates, and which can be converted to the diisocyanates which are valuable monomers, which are of value in the synthesis of polyimides and polyamides. The acids may also be reduced to alcohols and aldehydes by well known to the art procedures.

Once produced, the 2,3,9,10-tetramethyl precursor (II) in Scheme 1 may be readily oxidized to 12,14-(R)$_2$-12,14-(R$_f$)$_2$-12H,14H-5,7-dioxapentacene-2,3,9,10-tetracarboxylic acids, which in turn may be thermally dehydrated to the corresponding 2,3,9,10-dianhydride (III). The dianhydride (III) may in sequence be polymerized with a diamine, such as for example 4,4'-diaminodiphenyl ether, or 3,4'-diaminodiphenyl ether, in order to form a respective polyamic acid, which may be then dehydrated either chemically or thermally to form the corresponding polyimide. Reaction to polyimide, of course, may be performed without isolating the polyamic acid first in a manner for example shown in Examples 14 to 17.

Oxidation of the tetramethyl precursor to the tetraacid may be performed by using potassium permanganate. Other methods, such as Mn/Co catalyzed oxidation with oxygen, or with air, or oxidation with nitric acid may also be employed. Conversion of the tetraacid to the dianhydride may be effected thermally, or by boiling in acetic anhydride, or by heating a slurry of the tetraacid in chloroform with excess thionyl chloride. Thermal conversion at 220° C. overnight is preferred.

In a similar fashion, as shown in scheme 2, the dimethyl precursor (V) 12,14-diphenyl-12,14-bis (trifluoromethyl-2,10-dimethyl-12H,14H-5,7-dioxapentacene may be oxidized to 12,14-diphenyl-12,14-bis (trifluoromethyl)-12H,14H-5,7-dioxapentacene-2,10-dicarboxylic acid (VI), and then reacted with thionyl chloride to provide 12,14-diphenyl-12,14-bis (trifluoromethyl)-12H,14H-5,7-dioxapentacene-2,10-dicarbonyl dichloride (VII). This diacid dichloride may be subsequently reacted with sodium azide by the Curtius reaction to provide 12,14-diphenyl-12,14-bis (trifluoromethyl)-12H,14H-5,7-dioxapentacene-2,10-diisocyanate (IX), through the intermediate (VII). The diisocyanate (IX) may be hydrolyzed to by well known to the art methods to form 12,14-diphenyl-12,14-bis (trifluoromethyl)-12H,14H-5,7-dioxapentacene-2,10-diamine (X).

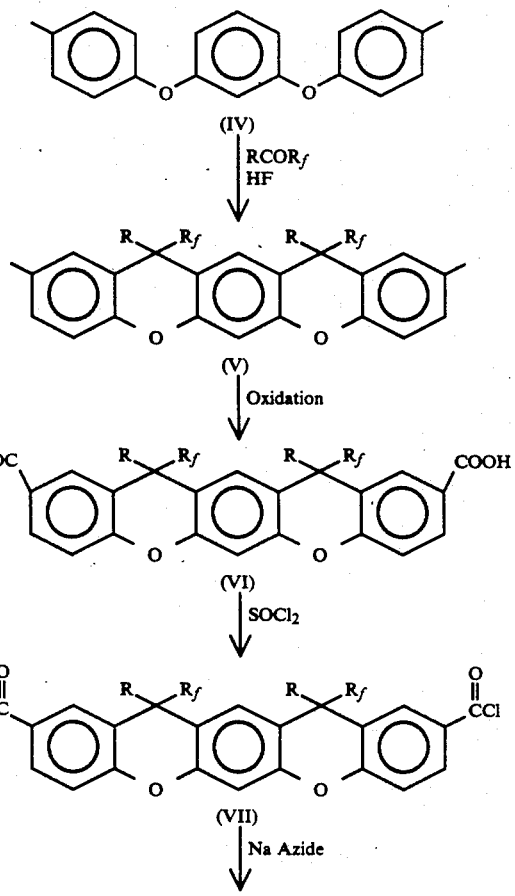

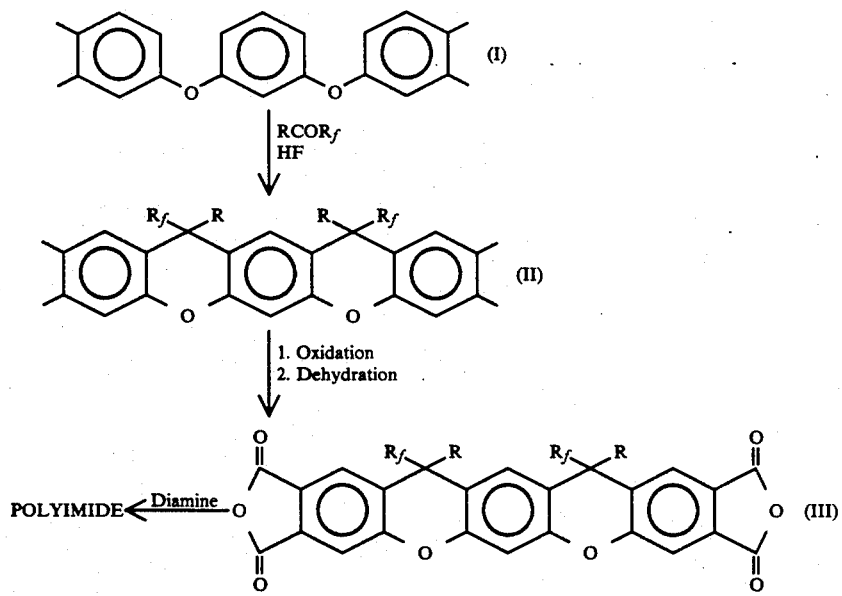

-continued
SCHEME 2

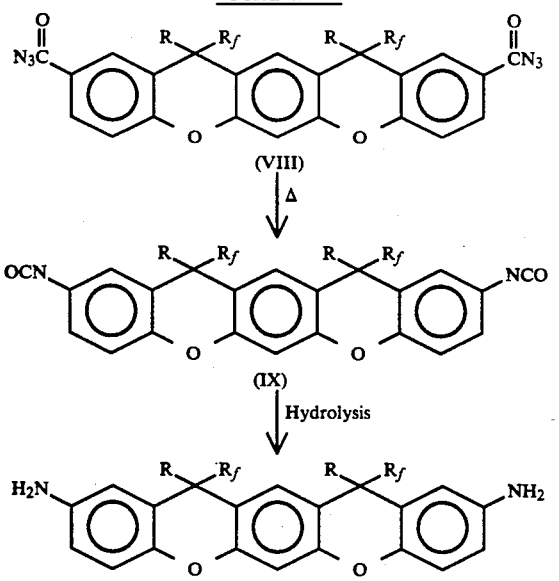

Using similar synthetic approaches as those described in the Examples, different isomer structures, such as for example the ones shown below may be made.

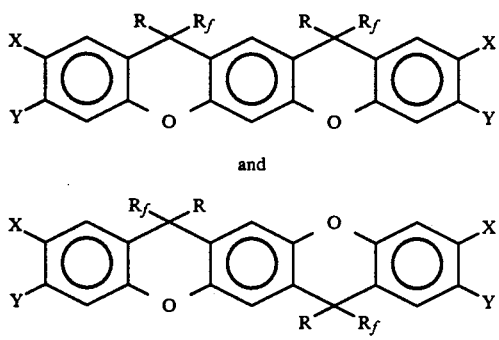

and

Also, cis- and trans- isomers are possible when R is different than $R_f$.

Examples of polyimides encompassed by the present invention include those having the recurring structural unit

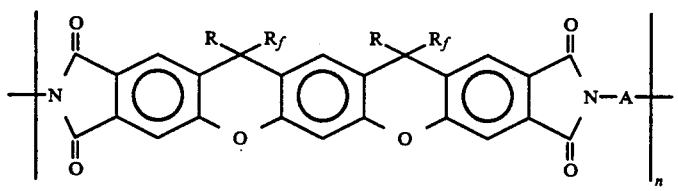

as well as structures comprising the isomeric forms, wherein R is selected from the group consisting of aryl, substituted aryl and perfluoroalkyl of 1 to 16 carbon atoms; $R_f$ is perfluoroalkyl of 1 to 16 carbon atoms (and more preferably 1 to 8 carbon atoms); A is a divalent radical containing at least two carbon atoms, each of the two nitrogen atoms being attached to a different carbon atom of divalent radical; and n is a positive integer.

The polyimides made with monomers of this invention display outstanding properties, which make them useful as either coatings or shaped structures such as self-supporting films, fibers and filaments, or both. Such polyimides may be generally prepared by reacting dianhydrides (III) for example with a diamine, preferably aromatic, in an inert organic solvent to form a polyamic acid solution and subsequently converting the polyamic acid to polyimide as described for example in U.S. Pat. No. 3,179,614; U.S. Pat. No. 3,179,630 and U.S. Pat. No. 3,179,634, the disclosures of which are incorporated herein by reference. Direct synthesis by thermally imidizing the respective poly(amic acid) is of preference in many occasions, as polyimides of the present invention may be soluble in such solvents as N-methyl-2-pyrrolidone, N-cyclohexyl-2-pyrrolidone and the like. It was unexpected to see very stiff polyimides characterized by high Tg, as the ones described for example in Example 14 of the present invention to exhibit also a high degree of solubility.

If desired, dianhydrides, such as (III) for example, may also be blended with from 15 to 85 mole % of other dianhydrides, such as pyromellitic dianhydride; 2,3,6,7-naphthalene tetracarboxylic dianhydride; 3,3',4,4'-biphenyl tetracarboxylic dianhydride; 1,2,5,6-naphthalene tetracarboxylic dianhydride; 2,2',3,3'-biphenyl tetracarboxylic dianhydride; 3,3',4,4'-benzophenone tetracarboxylic dianhydride; 2,2-bis(3,4-dicarboxyphenyl) propane dianhydride; bis(3,4-dicarboxyphenyl) sulfone dianhydride; 3,4,9,10-perylene tetracarboxylic dianhydride; bis(3,4-dicarboxyphenyl)propane dianhydride; 1,1-bis-(2,3-dicarboxyphenyl)ethane dianhydride; 1,1-bis-(3,4-dicarboxyphenyl)ethane dianhydride; bis-(2,3-dicarboxyphenyl)methane dianhydride; bis-(3,4-dicarboxyphenyl)methane dianhydride; oxydiphthalic dianhydride; bis (3,4-dicarboxyphenyl)sulfone dianhydride; and the like.

Suitable diamines for use in the polyimide compositions of the invention include such diamines as for example (X) in Scheme 2, which is a direct product of this invention. Examples of other suitable diamines are:
diaminodurene;
2,2'-trifluoromethylbenzidine meta-phenylenediamine;
paraphenylene diamine;
4,4'-diamino-diphenylpropane;
4,4'-diamino-diphenylmethane;
benzidine;
4,4'-diamino-diphenyl sulfide;
4,4'-diamino-diphenyl sulfone;
3,3'-diamino-diphenyl sulfone;
4,4'-diamino-diphenyl ether;
2,6-diamino-pyridine;
bis-(4-amino-phenyl)diethylsilane;
bis-(4-amino-phenyl)phosphine oxide;
bis-(4-amino-phenyl)-N-methylamine;
1,5-diamino-naphthalene;
3,3'-dimethyl-4,4'-diamino-biphenyl;
3,3'-dimethoxy benzidine;
2,4-bis(beta-amino-t-butyl)toluene;
bis-(para-beta-amino-t-butyl-phenyl)ether;

para-bis(2-methyl-4-amino-pentylbenzene;
para-bis-(1,1-dimethyl-5-amino-pentyl)benzene;
m-xylylene diamine;
p-xylylene diamine;
bis(para-amino-cyclohexyl)methane;
hexamethylene diamine;
heptamethylene diamine;
octamethylene diamine;
nonamethylene diamine;
decamethylene diamine;
3-methylheptamethylene diamine;
4,4-dimethylheptamethylene diamine;
2,11-diamino-dodecane;
1,2-bis-(3-amino-propoxy)ethane;
2,2-dimethyl propylene diamine;
3-methoxy-hexamethylene diamine;
2,5-dimethylhexamethylene diamine;
2,5-dimethylheptamethylene diamine;
5-methylnonamethylene diamine;
1,4-diamino-cyclohexane;
1,12-diamino-octadecane;
$H_2N(CH_2)_3O(CH_2)_3NH_2$;
$H_2N(CH_2)_3S(CH_2)_3NH_2$;
$H_2N(CH_2)_3N(CH_3)(CH_2)_3NH_2$;
and mixtures thereof.

Examples of useful solvents include liquid N,N-dialkylcarboxylamides, generally. Preferred solvents include the lower molecular weight members of such carboxylamides, particularly N,N-dimethylformamide and N,N-dimethylacetamide. Other useful compounds of this class of solvents are N,N-diethylformamide and N,N-diethylacetamide. Other solvents which may be used are dimethylsulfoxide, N-methyl-2-pyrrolidone, N-cyclohexyl-2-pyrrolidone, 1,3-dimethyl-2-imidozolidione, N-vinyl-2-pyrrolidone, and the like, tetramethylurea, dimethylsulfone, hexamethylphosphoramide, tetramethylene sulfone, and the like. Other examples of solvents in the preparation of the compositions of the present invention are sulfoxide type solvents including dimethylsulfoxide, diethylsulfoxide, and the like, phenolic solvents including phenol, o-, m-, p-cresol, xylenol, halogenated phenol, catechol, and the like, and a number of lactones including 7-butyrolactones. These solvents may be used alone or as a mixture. Partial use of aromatic hydrocarbons such as xylene, toluene, and the like, is also possible. The solvents can be used alone, in combinations with one another or in combinations with poor solvents such as benzene, benzonitrile, dioxane, etc. The amount of solvent used preferably ranges from 75 to 90 weight % of the polyamic acid, since this concentration has been found to give optimum molecular weight.

Conversion of the polyamic acid to polyimide can be accomplished by either a thermal conversion or a chemical conversion process. According to the thermal conversion process, the polyamic acid solution may be cast on a heated conversion surface, such as a metal drum or belt, and heated at a temperature of above about 50° C. to partially convert the polyamic acid to polyimide. The extent of polyamic acid conversion depends on the temperature employed and the time of exposure, but, generally about 25 to 95% of amic acid groups are converted to imide groups. The partially converted polyamic acid is then heated at or above 220° C. to obtain complete conversion to the polyimide.

In the chemical conversion process, the polyamic acid solution may be first chilled to about 10° C. to −10° C. and polyamic acid conversion chemicals are added. The polyamic acid conversion chemicals are tertiary amine catalysts and anhydride dehydrating materials. The preferred anhydride dehydrating material is acetic anhydride and is used in excess of the amount of amic acid groups in the polyamic acid, typically about 2–2.5 moles per equivalent of polyamic acid. A comparable amount of tertiary amine catalyst may be used. Besides acetic anhydride, other operable lower fatty acid anhydrides include propionic, butyric, valeric, mixed anhydrides of these with one another and with anhydrides of aromatic monocarboxylic acids, for example, benzoic acid, naphthoic acid, and the like, and with anhydrides of carbonic and formic acids, as well as aliphatic ketenes (ketene and dimethyl ketene). Ketenes may be regarded as anhydrides of carboxylic acids derived from drastic dehydration of the acids.

The preferred tertiary amine catalysts are pyridine and beta-picoline and they are used in an amount of about one mole per mole of anhydride dehydrating material. Tertiary amines having approximately the same activity as the preferred pyridine and beta-picoline may also be used. These include 3,4-lutidine; 3,5-lutidine; 4-methylpyridine; 4-isopropylpyridine; N-dimethylbenzylamine; isoquinoline; 4-benzylpyridine, and N-dimethyldodecylamine. Trimethylamine and triethylamine are more active than those amines listed above and can be used in smaller amounts.

The polyamic acid conversion chemicals react at about room temperature or above to convert polyamic acid to polyimide. The chemical conversion reaction occurs at temperatures from 10° to 120° C., with the reaction being very rapid at the higher temperatures and very slow at the lower temperatures. Below a certain temperature, polyamic acid chemical conversion comes to a practical halt. This temperature is generally about 10° C. It is important, therefore, that the polyamic acid solution be chilled below this temperature before adding the polyamic acid conversion chemicals and that the temperature of the solution, with conversion chemicals, be maintained below this temperature during extrusion or casting.

The treated, chilled, polyamic acid solution is coated, cast or extruded onto a heated conversion surface whereupon some of the solvent is evaporated from the solution, the polyamic acid is partially chemically converted to polyimide, and the solution takes the form of a polyamic acid-polyimide gel. Conversion of amic acid groups to imide groups depends on contact time and temperature but is usually about 25 to 95% complete. The gel is subsequently dried to remove the water, residual solvent, and remaining conversion chemicals, and the polyamic acid is completely converted to polyimide. The drying can be conducted at relatively mild conditions without complete conversion of polyamic acid to polyimide at that time, or the drying and conversion can be conducted at the same time using higher temperatures. Preferably, high temperatures are used for short times to dry the film and convert it to polyimide in the same step. It is preferred to heat the film to a temperature of 200–450° C. for 15 to 400 seconds.

The dianhydrides, diacid chlorides, diacids, diisocyanates and diamine monomers of the present invention may be used to prepare polyimides, polyamides, polyesters, polycarbonates, polyurethanes polyureas, and the like, by techniques which are well-known in the art.

The new monomers have, for example in the case of polyimides derived therefrom, a larger separation between the polar groups, as compared with the existing dianhydrides (including perfluoroalkyl and aryl perfluoroalkyl xanthenes as described in our co-pending application No. 07/527,740). The distance between imide nitrogens in the case of polyimides made according to the present invention is about 17A, while it is only about 11–12A in the case of tricyclic xanthene analogs, and even less in the case of pyromellitic dianhydride. Typically, the greater the distance between the polar groups the lower the dielectric constant, and the lower the water absorption, both features being highly desirable in polyimides. Another important property for many applications of polyimides is the coefficient of thermal expansion, which preferably should match as close as possible the coefficient of thermal expansion of the substrate on which the polyimide is to be applied. The polyimides of the present invention seem to have coefficients of expansion suitable for substrates employed in electronics, as well as other applications.

Since the monomers of the present invention possess two, rather than one, fluorinated bridges, they also have higher fluorine to anhydride ratio, as compared to their tricyclic perfluoroalkyl xanthene analogs, or to other well known in the art dianhydrides, such as 6FDA (2,2'-bis(3,4-dicarboxyphenyl) hexafluoropropane).

The following examples illustrate, but do not limit, the instant invention. All parts and percentages are by weight unless otherwise indicated.

All reagents used were commercial materials, unless otherwise indicated. IR spectra were measured as Nujol mulls, or as poly ′le films, on a Perkin-Elmer Grating IR Spectrophot⌣ .er Model 457. NMR spectra were determined on the GE QE-300 instrument, using deuterochloroform as solvent and tetramethylsilane as internal standard.

The starting diethers 1,3-bis(3,4-dimethylphenoxy)-benzene and 1,4-bis(3,4-dimethylphenoxy)benzene were prepared from potassium 3,4-dimethylphenoxide and the corresponding 1,3- or 1,4-dibromobenzenes, according to M. M. Koton and F. S. Florinskii, Zh. Org. Khim, 4, 774–776 (1969). Using p-cresol instead of 3,4-dimethylphenol in the above reactions will yield 1,3-bis(4-methylphenoxy)benzene and 1,4-bis(4-methylphenoxy)benzene. Other chemicals were commercial reagents.

EXAMPLE 1

2,3,9,10-Tetramethyl-12,12,14,14-tetrakis-(trifluoromethyl) -12H,14H-5,7-dioxapentacene

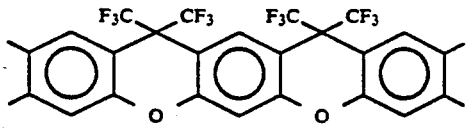

A mixture of 128 g (0.4 mole) of 1,3 bis(3,4 dimethylphenoxy)benzene, 136 g (0.4 mole HFA and 240 g (12 moles) HF was heated in an autoclave at 150 for 8 hours. The reaction mixture was poured into excess ice-cold aqueous alkali, and extracted with 2 L of methylene chloride. The extracts were filtered through a layer of alumina, and stripped. The residue was stirred with methanol, and was filtered, yielding 25 g of solid. From evaporation of the filtrate, followed by short-path vacuum distillation, and trituration of the glassy distillate with methanol/acetone another 9 g of the product was obtained, for a total yield of 34 g (14%). The product was recrystallized from toluene/heptane, and the analytical sample was sublimed at 250/1 Torr; m.p. 242–243° C. NMR: singlets at 8.47(b), 7.58(b), 7.02, 6.93, and 2.30 ppm in 1:2:2:1:6 ratio. Analysis: calc. for $C_{28}H_{18}F_{12}O_2$: C 54.7; H 2.93; F 37.1; found: C 52.9; H 2.74; F 37.4%.

The structure of 2,3,9,10-tetramethyl-12,12,14,14-tetrakis(trifluoromethyl) -12H,14H,5,7-dioxapentacene has been determined by single crystal X-ray crystallography. The material was crystallized from chloroform as a monosolvate, in orthorhombic form. The structure is shown below. The molecule is planar, and bent in a "banana" shape, as a result of the difference between the C—O and C—C ring junction distances (1.364°). The trifluoromethyl groups are eclipsed. The angle between the vector bisecting the dimethyl ring sides is 21.7°, and this would correspond to the angle between the $(CO)_2N$—C bonds in polyimides, obtained from the derived dianhydride. Based on this X-ray structure, the distance between the N atoms in derived polyimides would be about 16.7 A, which is substantially longer than in those derived from an analogous tricyclic system (about 12 A), or from other common dianhydrides, which should lead to an improvement in the dielectric constant and water absorption properties.

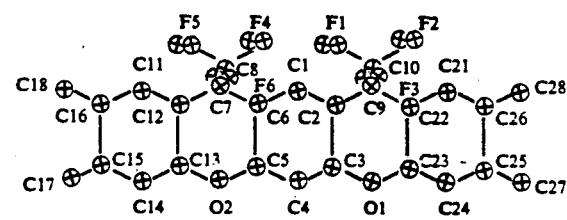

EXAMPLE 2

12,12,14,14-Tetrakis(trifluoromethyl)-12H,14H 5,7-dioxapentacene -2,3,9,10-tetracarboxylic Dianhydride

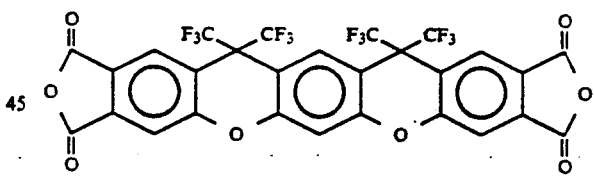

In a 1-L four-neck flask, a mixture of 30.7 g (0.05 mole) of the compound prepared in Example 1, 400 ml pyridine and 100 ml water was stirred mechanically, and heated to reflux. Solid $KMnO_4$ (60 g, 0.38 mole) was added in portions over 30 min. After 1.5 hour of reflux, the slurry was filtered through a bed of Celite ®, and the filter cake was washed with two 50 ml portions of 4:1 pyridine/water mixture. The combined filtrates were concentrated to one half the original volume (some surfactant had to be added to reduce foaming), and reoxidized as above with another 60 g portion of $KMnO_4$, having added beforehand 50 ml of 50% NaOH and water to bring the volume to the half mark of the flask. After refluxing again for 1.5 hour, the mixture was filtered through Celite ®, and was acidified with sulfuric acid. A white solid was obtained which filtered very slowly (two days); it was washed with hot water, and dried. It was then boiled in acetic anhydride, and recrystallized from it. The compound is sublimable in vacuo. Analysis: calc. for $C_{28}H_6F_{12}O_8$: C 48.1; H 0.86; found: C 48.2; H 1.06%.

EXAMPLE 3

12,14-Diphenyl-12,14-bis(trifluoromethyl)-12H,14H-5,7-dioxa -2,3,9,10-tetramethylpentacene

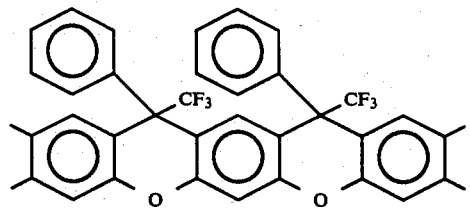

A mixture of 91.4 g (0.287 mole) 1,3-bis(3,4-dimethylphenoxy)benzene, 100 g (0.575 mole) trifluoroacetylbenzene, and 180 g (9 moles) HF was heated in an autoclave for 8 hours at 130° C. The shaker tube contents were transferred into a polyethylene jar containing ice-water slurry and 300 ml 50% NaOH. The product was extracted with methylene chloride, the extracts were passed through a short alumina layer, and stripped down to 500 ml. The slurry was stirred with methanol plus 50 ml acetone, and was filtered, yielding 87 g (50%) of creamy solid, which was recrystallized from toluene. The initial melting range was wide (sintering around 245, melting 255–260° C.), implying presence of cis-trans isomers. One recrystallization from toluene gave 55 g of solid, which sintered at 257, and melted 258–265° C. After several recrystallizations from toluene the m.p. rose to 287–289° C., presumably indicating a single isomer. NMR: m 7.07, s 6.98, s 6.94, s 6.55, s 6.17, s 2.25, s 2.06 in 10:2:1:2:1:6:6 ratio. Analysis: calc. for $C_{38}H_{28}F_6O_2$: C 72.4; H 4.44; F 18.1; found: C 72.5; H 4.88; F 18.6%.

EXAMPLE 4

12,14-Diphenyl-12,14-bis(trifluoromethyl)-12H,14H-5,7-dioxapentacene -2,3,9,10-tetracarboxylic Dianhydride

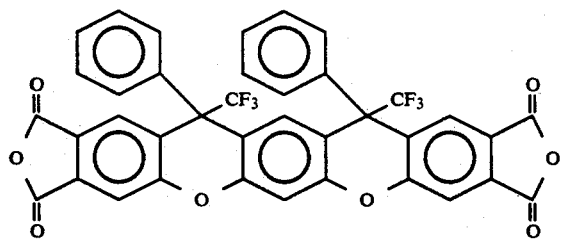

Oxidation of the compound prepared in Example 3 was carried out on a 31.5 g (0.05 mole) sample, by using the technique described in Example 2. The tetraacid, 12,14-Diphenyl -12,14-bis(trifluoromethyl)-12H,14H-5,7-dioxapentacene -2,3,9,10-tetracarboxylic dianhydride, was isolated by filtration after acidification of the final oxidation filtrate with sulfuric acid, and washed thoroughly with water. When still moist, it was boiled briefly in 500 ml acetic anhydride, filtered through Celite ®, and stripped. The product was recrystallized from a mixture of anisole and acetic anhydride (300 ml/50 ml for 35 g of crude product), using Darco, and filtering through Celite ®. A 13.5–14.5 g first crop was obtained, which did not melt up to 330° C. from the filtrate a second crop of about 13.5 g was obtained which melted partly in the 320–330° C. range and was probably a mixture of isomers. The first crop had low solubility in chloroform, but sufficient for obtaining an NMR spectrum; the second crop was very soluble. NMR of the first crop indicated a single isomer: s 7.84, broader s 7.57, m 7.3–7.4, s 7.24, broad d 7.17 and broad s 6.37 ppm in 2:2:6:1:4:1 ratio. The second crop contained the above isomer in 35–40% amount, but was mostly the other isomer, characterized by a proton peak at 6.26 ppm. Analysis of the first crop: calc. for $C_{38}H_{14}F_6O_8$: C 64.0; H 1.97; found: C 64.0; H 2.25.

EXAMPLE 5

2,3,9,10-Tetramethyl-5,12-diphenyl-5,12-bis(trifluoromethyl)-5H,12H-7,14-dioxapentacene

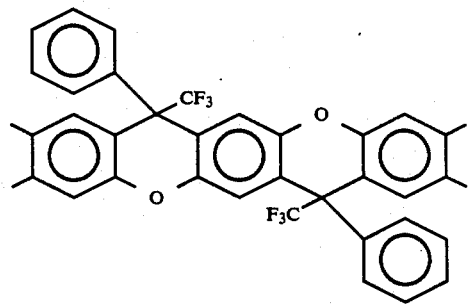

A mixture of 45.7 g (0.144 mole) 1,4-bis(3,4 dimethylphenoxy)benzene, 50.0 g (0.288 mole) trifluoroacetylbenzene, and 90 g (4.5 mole) HF was shaken in an autoclave at 120° C. for 8 hours. The clave contents were transferred to a polyethylene jar, half filled with ice-water, and containing 250 ml 50% NaOH. Methylene chloride was added, the slurry was filtered through Celite ®, the organic layer was separated and the extracts were stripped. The residue was stirred with acetone and filtered, yielding 19.4 g of white solid. Because of its low solubility in methylene chloride, some product was lost on the Celite ® pad. The IR was sharp, and the NMR was consistent with structure: m 7.33–7.45, 2 s 6.85, 2 s 6.67, s 6.55, 2 s 2.21, s 2.07 ppm in 5:1:1:1:3:3 ratio, indicating presence of cis-trans isomers. Analysis: calc. for $C_{38}H_{28}F_6O_2$: C 72.4; H 4.44; found: C 71.3; H 4.57%.

EXAMPLE 6

5,12-diphenyl-5,12-bis(trifluoromethyl)-5H,12H-7,14-dioxapentacene -2,3,9,10-tetracarboxylic anhydride Oxidation of the compound prepared in Example 5 to the corresponding dianhydride was carried out on a 63-g sample by using using 116 g potassium permanganate, as described in Example 2. After acidification of the final alkaline solution, filtration, washing and drying there was obtained 2.6 g of a white solid, 5,12-diphenyl -5,12-bis(trifluoromethyl)-5H,12H-7,14-dioxapentacene -2,3,9,10-tetracarboxylic acid. An IR spectrum indicated presence of COOH groups.

EXAMPLE 7

Polyimide of 12,14-Diphenyl-12,14-bix(trifluoromethyl)-12H, 14H-5,7-dioxa-pentacene-2,3,9,10-tetracarboxylic Dianhydride with paraphenylenediamine To a solution of 1.052 g p-phenylenediamine in 42 ml dry NMP there were added in portions, at room temperature, 6.948 g of 12,14-Diphenyl-12,14-bis (trifluoromethyl)-12H,14H-5,7-dioxapentacene-2,3,9,10-tetracarboxylic dianhydride. The solution turned yellow, then green, and became viscous as the corresponding poly(amic acid) formed.

EXAMPLE 8

Polyimide of 12,14-Diphenyl-12,14-bis(trifluoromethyl)-12H, 14H-5,7-dioxapentacene-2,3,9,10-tetracarboxylic Dianhydride with 4,4'-diaminodiphenyl ether To a solution of 1.313 g 4,4'-diaminodiphenyl ether in 40 ml dry NMP, there were added, in portions, 4.687 g of 12,14-diphenyl-12,14-bis(trifluoromethyl)-12H,14H-5,7-dioxapentacene-2,3,9,10-tetracarboxylic dianhydride, at room temperature. It dissolved fairly quickly, and the solution became viscous, due to the formation of the corresponding poly(amic acid).

EXAMPLE 9

2,3,9,10-Tetramethyl-12,14-diphenyl-12,14-bis (pentafluoroethyl)-12H,14H-5,7-dioxapentacene A mixture of 196 g (0.61 mole) of 1,3-bis(3,4-dimethylphenoxy)benzene, 275 g (1.23 mole) phenyl pentrafluoroethyl ketone, and 320 g (16 moles) HF was heated in an autoclave for 8 hours at 140° C. After cooling, and venting off excess HF, the autoclave contents were transferred to a 1-gallon polyethylene jar, half filled with ice water, and containing 500 ml of 50 % sodium hydroxide. The autoclave was rinsed out with methylene chloride, and the washings were added to the jar. The product was extracted with methylene chloride, the extracts were filtered through a layer of alumina, and the solvent was stripped off at atmospheric pressure yielding a syrup. This residue was stirred with acetone, yielding 63 g of a solid, m p. 270-281° C. (with prior softening) after recrystallization from toluene. Evaporation of the filtrate, and stirring with isopropyl alcohol gave a second crop of 48 g, m.p. 228-233° C. (with prior softening), after recrystallization from toluene/heptane. Total yield 111 g (25%). The IR spectra of both fractions were essentially identical, representing mixtures of cis- and trans-isomers. NMR: Aromatic multiplet with peaks at 7.22, 7.1, 7.0, s 6.93, s 6.87, broad s 6.63, broad s 6.40 in 10 (total multiplet):2:1:2:1:6:6 ratio. Analysis: calc. for $C_{40}H_{28}F_{10}O_2$: C 65.8, H 3.84, F 26.0; found: C 65.8; H 3.55; F 26.1 %.

EXAMPLE 10

12,14-Diphenyl-12,14-bis(pentafluoroethyl)-12H,14H-5,7-dioxapentacene -2,3,9,10-tetracarboxylic acid and 12,14-Diphenyl -12,14-bis(pentafluoroethyl)-12H,14H-5,7-dioxapentacene -2,3,9,10dianhydride The oxidation was done as described before for the trifluoromethyl analog in Example 4, using 100 g of 2,3,9,10-Tetramethyl-12,14-diphenyl-12,14-bis(pentafluoroethyl) -12H,14H-5,7-dioxapentacene and 160 g potassium permanganate per oxidation step. After final acidification with sulfuric acid, there was obtained a tacky, creamy-white solid, which solidified on cooling. It was filtered off, boiled in 1 L water, cooled and filtered again. There was obtained 55.6 g (48 %) of the tetraacid. The tetraacid was boiled in 300 ml acetic anhydride, cooled, and the precipitated solid was filtered yielding 6.7 g of dianhydride, characterized by anhydride peaks in the IR at 1850 and 1785 cm$^{-1}$.

EXAMPLE 11

2,3,9,10-Tetramethyl-12,14-diphenyl-12,14-bis (heptafluoropropyl)-12H,14H-5,7-dioxapentacene A mixture of 159 g (0.5 mole) 1,3-bis(3,4-dimethylphenoxy)benzene, 274 g (1.0 mole) phenyl heptafluoropropyl ketone, and 280 g (14 moles) HF was heated in an autoclave for 8 hours at 140° C. After cooling, and venting off excess HF, the autoclave contents were transferred to a 1-gallon polyethylene jar, half filled with ice water, and containing 500 ml of 50% sodium hydroxide. The autoclave was rinsed out with methylene chloride, and the washings were added to the jar. The product was extracted with methylene chloride, the extracts were filtered through a layer of alumina, and the solvent was stripped off at atmospheric pressure yielding 312 g of a taffy-like residue, which was very soluble in acetone. The residue was extracted with several 500 ml portions of boiling methanol, and then was stirred with isopropyl alcohol, producing a solid in 21.3 g (5.1 % yield) with a sharp IR spectrum, devoid of OH bands, and melting in the 198-220° C. range, and after recrystallization from heptane at 237-238° C. NMR of the product melting over the wide range showed presence of cis- and trans- isomers: aromatic protons as multiplets 7.05-7.25, 6.85-7.0, broad s 6.66, two broad singlets at 6.58 and 6.50, and methyl singlets at 2.20 and 2.02 ppm in 6:7:2:1(total of the 6.58 and 6.50 peaks): 6:6 ratio. The recrystallized material was a single isomer, by NMR m 7.1, m 7.0, s 6.94, s 6.86, broad s 6.65, broad s 6.47, s 2.23 and s 2.04 ppm in 4:6:2:1:2:1:6:6 ratio. Analysis: calc. for $C_{42}H_{28}F_{14}O_2$: C 60.7; H 3.37, F 32.0; F 32.0; found C 70.0; H 3.61, F 30.1%.

EXAMPLE 12

2,3,9,10-Tetramethyl-12,14-bis(3-trifluoromethylphenyl-12,14-bis (trifluoromethyl)-12H,14H-5,7-dioxapentacene A mixture of 131 g (0.41 mole) 1,3-bis(3,4-dimethylphenoxy) -benzene, 200 g (0.82 mole) 3-trifluoromethylphenyl trifluoromethyl ketone, and 220 g (11 moles) HF was heated in an autoclave for 8 hours at 140° C. After cooling, and venting off excess HF, the autoclave contents were transferred to a 1-gallon polyethylene jar, half filled with ice water, and containing 500 ml of 50 % sodium hydroxide. The autoclave was rinsed out with methylene chloride, and the washings were added to the jar. The product was extracted with methylene chloride, the extracts were filtered through a layer of alumina, and the solvent was stripped off at atmospheric pressure. The residue was stirred with 300 ml acetone yielding 30 g of solid. Addition of methanol to the filtrate gave another 31 g of solid. Each was chouromatographed on alumina, and this removed reddish impurities. Each of these fraction was a mixture of cis- and trans- isomers in different proportions. The first fraction was about 2:1 in the less soluble isomer, while the second was about 3:2 in the more soluble isomer. NMR of the first fraction: m 7.15-7.60; s 7.02 (s+s) 6.99, 6.98; (s+s) 6.53, 6.48; broad (s+s) 5.98, 5.95; s 2.25, (s+s) 2.07, 2.06 ppm in 8:2:1:2:1:6:6 ratio. The NMR spectrum of the second fraction was identical, except that the underlined peaks were in different ratios, corresponding to the proportions of the cis- and trans- isomers. Analysis: calcd. for $D_{40}H_{26}F_{12}O_2$: C 62.7; H 3.39; F 29.8; found: C 61.7, H 3.75; F 28.7%.

EXAMPLE 13

12,14-Diphenyl-12,14-bis(trifluoromethyl)-12H, 14H-5,7-dioxapentacene

A mixture of 20 g (0.03 mole) 12,14-Diphenyl-12,14-bis(trifluoromethyl) -12H,14H-5,7-dioxapentacene-2,3,9,10-tetracarboxylic acid, 25 g copper powder and 100 ml quinoline was refluxed vigorously for 4 hours. The cooled mixture was poured into a cold solution of 30 ml concentrated HCl in 300 ml water. The product was extracted with methylene chloride, and the extracts were passed through a column of alumina, and the eluate was stripped. The residue was stirred with methanol, and was filtered yielding 2.5 g (16 %) of a solid in two crops. The crude material melted at 203-213° C., in line with the presence of cis- and trans- isomers. The title compound was purified by vacuum sublimation at 0.6 Torr and 200° C., and melted then at 209-215° C. Analysis: Calc. for $C_{34}H_{20}F_6O_2$: C 71.1; H 3.48, F 19.9; found: C 71.4; H 3.65; F 19.9 %. The mass spectrum showed presence of two isomers in about 2:1 ratio, and a parent peak at 574, with peaks at 505 and 436 m/e showing loss of one and two $CF_3$ groups, respectively. The NMR spectrum had complex multiplets in the 7.2-7.35 and 6.9-7.1 ppm range (totaling 17 Hs), plus two pairs of broad singlets at 6.86+6.84 ppm (2H) and 6.32+6.22 ppm (1H). The coefficient of thermal expansion (CTE) was found to be 34 ppm (0-200° C.) by thermomechanical analysis (TMA) at 10° C. per minute.

EXAMPLE 14

Polyimide from 12,14-Diphenyl-12,14-bis (trifluoromethyl)-12H,14H-5,7-dioxapentacene-2,3,9,10-tetracarboxylic dianhydride and 4,4'-diaminodiphenyl ether Into a 100 ml reaction kettle fitted with a nitrogen inlet, mechanical stirrer, and a Dean-Stark trap with condenser were charged 6.2488 g (8.745 mmol) of 12,14-diphenyl-12,14-bis(trifluoromethyl)-12H,14H-5,7-dioxapentacene-2,3,9,10-tetracarboxylic dianhydride and 1.7512 g (8.745 mmol) of 4,4'-diaminodiphenyl ether. Shortly thereafter, 25.6 ml of N-methyl-2-pyrrolidone and 6.4 ml of N-cyclohexyl-2-pyrrolidone were added, and stirring was begun. As the monomers dissolved and reacted, the reaction mixture warmed slightly. The temperature was maintained at room temperature for several hours and then the reaction mixture was raised to a temperature of 180-190° C. Finally, the reaction was allowed to proceed overnight (about 16 hours) to imidize the polymer. After cooling, the polymer solution was slowly pressure-filtered through a 1 micron filter and then spin-coated onto a 5" silicon wafer. After spin coating, the wafer was immediately placed in a oven at 135° C. for 30 min., then placed into another oven and heated to 200° C. for 30 min and 350° C. for 1 hour. The resulting polyimide film was coherent and adhered well to the wafer. Etching of the oxide layer of the silicon in aqueous HF, yielded the free standing polyimide film which was pale yellow in color and creasable. The 11.1 micron film gave the following mechanical properties when tested on an Instron Model 4501 per ASTM D 882-83 (Method A): Tensile Strength=133 MPa, Tensile Elongation at Break=32%, and Young's Modulus=2.0 GPa.

EXAMPLE 15

Polyimide from 12,14-Diphenyl-12,14-bis (trifluoromethyl)-12H,14H-5,7-dioxapentacene-2,3,9,10-tetracarboxylic dianhydride and 4,4'-diaminodiphenyl ether Similar to the procedure given in Example 14, a polymer was prepared from 12,14-Diphenyl-12,14-bis (trifluoromethyl)-12H,14H-5,7-dioxapentacene-2,3,9,10-tetracarboxylic dianhydride and 4,4'-diaminodiphenyl ether, except that 32 ml of N-methyl-2-pyrrolidone was used as sole reaction solvent and the reaction was allowed to proceed overnight at room temperature with no high temperature imidization step. The poly(amic acid) solution obtained was filtered through a 1 micron filter, spin coated and then cured to the polyimide under the same temperature profile as in Example 14. Properties of the imidized film were similar to those given in Example A: Tensile Strength=124 MPa, Tensile Elongation at Break=34%, and Young's Modulus=1.9 GPa. Dielectric constant of dry film at 1 MHertz was 2.6.

EXAMPLE 16

Polyimide from 12,14-Diphenyl-12,14-bis (trifluoromethyl)-12H,14H-5,7-dioxapentacene-2,3,9,10-tetracarboxylic dianhydride and diaminodurene Similar to the procedure given in Example 14, a polymer was prepared from 6.5047 g (9.1035 mmol) 12,14-diphenyl -12,14-bis(trifluoromethyl)-12H,14H-5,7-dioxapentacene -2,3,9,10-tetracarboxylic dianhydride and 1.4953 g (9.1035 mmol) diaminodurene (DAD) in 33.6 ml N-methyl -2-pyrrolidone (NMP) and 8.4 ml N-cyclohexyl-2-pyrrolidone (CHP). After dissolution, the reaction was allowed to proceed overnight at room temperature and then was heated to 180-190° C. to imidize the polymer. After letting the reaction proceed overnight at 180-90° C., the reaction was cooled to room temperature. A thick, yet soluble polyimide solution resulted which was then diluted with NMP and precipitated into methanol. After filtration and drying, the polyimide was dissolved in chloroform and precipitated once more into methanol. After filtration and drying, the polyimide was dissolved in tetrachloroethane (TCE) (~9% solids) and filtered through a 10 micron filter for spin coating onto silicon wafers.

Properties of an imidized film were: coefficient of linear Thermal Expansion (CTE)=27 ppm (0-200° C.); Tensil STrength=135 MPa; % Elongation=9; and Modulues-2.6 GPa. The dielectric constant of the dried film at 1 MegaHertz was 2.5.

EXAMPLE 17

Polyimide from 12,14-Diphenyl-12,14-bis (trifluoromethyl)-12H,14H-5,7-dioxapentacene-2,3,9,10-tetracarboxylic dianhydride and Bis(2,2'-trifluoromethyl) benzidine Similar to the procedure given in Example 14, a polymer was prepared from 5.5242 g (7.7312 mmol) 12,14-diphenyl -12,14-bis(trifluoromethyl)-12H,14H-5,7-dioxapentacene -2,3,9,10-tetracarboxylic dianhydride and 2.4758 g (7.7312 mmol) Bis(2,2'-trifluoromethyl)benzidine in 33.6 ml N-methyl-2-pyrrolidone (NMP) and 8.4 ml N-cyclohexyl-2-pyrrolidone (CHP). After dissolution, the reaction was allowed to proceed overnight at room temperature and then was heated to 180-190° C. to imidize the polymer. After letting the reaction proceed overnight at 180-190° C., the reaction was cooled to room temperature. A thick, yet soluble polymide solution resulted which was then diluted with NMP and precipitated into methanol. After filtration and drying, the polyimide was dissolved in chloroform and precipitated once more into methanol. After filtration and drying, the polyimide was dissolved in TCE (~12% solids) and filtered through a 10 micron filter for spin coating onto silicon wafers. The coefficient of Thermal Expansion of an imidzed film was found to be 10 ppm (0-200° C.).

What is claimed is:

1. A composition of matter comprising at least one of the isomeric structures having the formula

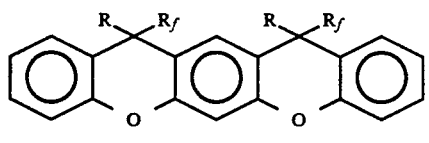

or

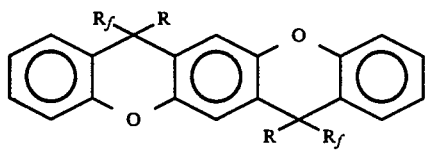

wherein R is selected from the group consisting of aryl, substituted aryl, and perfluoroalkyl; and $R_f$ is perfluoroalkyl.

2. The composition of claim 1 wherein R is $CF_3$ and $R_f$ is $CF_3$.

3. The composition of claim 1 wherein R is aryl, substituted aryl and $R_f$ is $CF_3$.

4. A composition of matter comprising at least one of the isomers having the formula

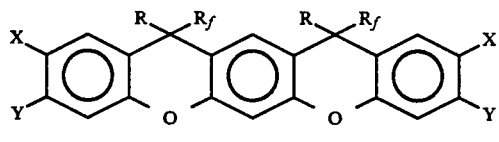

or

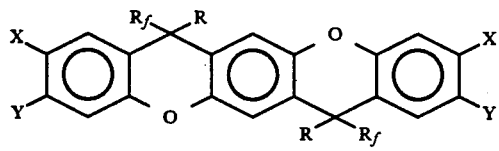

wherein R is selected from the group consisting of aryl, substituted aryl, and perfluoroalkyl; $R_f$ is perfluoroalkyl; X is selected from the group consisting of H, alkyl, COOH, COCl, $NH_2$, halogen, $SO_2$alkyl and NCO; Y is selected from the group consisting of X and OH; and X and Y on each phenolic ring are together —CO—O—CO—.

5. The composition of claim 4, wherein R is $CF_3$ and $R_f$ is $CF_3$.

6. The composition of claim 4, wherein R is aryl and $R_f$ is $CF_3$.

7. The composition of claim 4, wherein X and Y are $CH_3$.

8. The composition of claim 4 wherein X and Y are COOH.

9. The composition of claim 4 wherein each pair of X and Y on the same phenolic ring is —CO—O—CO—.

10. The composition of claim 4, wherein X is COOH and Y is H.

11. The composition of claim 4, wherein X is COCl and Y is H.

12. The composition of claim 4, wherein X is NCO and Y is H.

13. The composition of claim 4, wherein X is $NH_2$ and Y is H.

14. A process for preparing a composition comprising at least one of the monomers having the formula

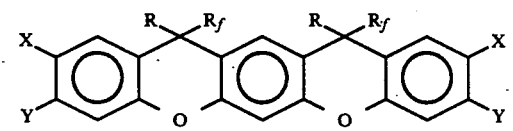

or

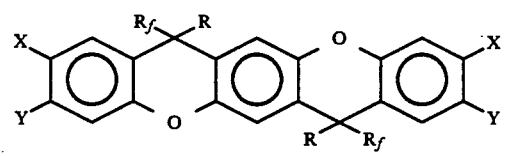

wherein R is selected from the group consisting of aryl, substituted aryl and perfluoroalkyl; $R_f$ is perfluoroalkyl; X is H or alkyl; and Y is H, alkyl, $NH_2$ or OH; comprising reacting $RCOR_f$ with a diether precursor having the formula

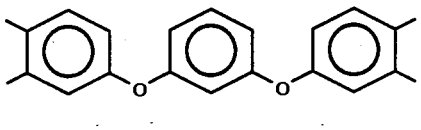

or

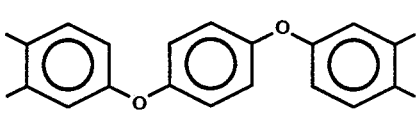

respectively, in hydrofluoric acid solvent at a temperature of from 110° C. to 180° C., wherein R, $R_f$, X and Y are as defined above, 15. The process of claim 14, wherein R is $CF_3$ and $R_f$ is $CF_3$.

16. The process of claim 14, wherein R is aryl and $R_f$ is $CF_3$.

17. The process of claim 14, wherein X and Y are $CH_3$.

18. The process of claim 14, wherein X $CH_3$ and Y is H.

19. A process for preparing a dianhydride composition of the formula

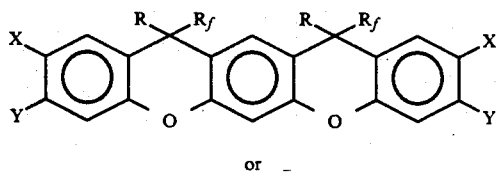

or

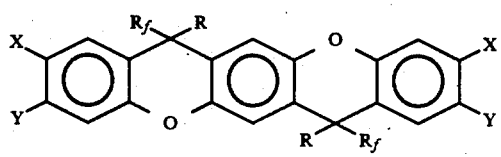

wherein R is selected from the group consisting of aryl, substituted aryl and perfluorOalkyl; $R_f$ is perfluoroalkyl; and X and Y together are —CO—O—CO—comprising (a) oxidizing a precursor having the above formula wherein both X and Y are $CH_3$ to form a tetraacid of the above formula wherein both X and Y are COOH; and (b) dehydrating the tetraacid to form the dianhydride.

20. The process of claim 14, wherein R is $CF_3$ and $R_f$ is $CF_3$.

21. The process of claim 14, wherein R is aryl and $R_f$ is $CF_3$.

22. A polyimide having the following recurring structural unit, including isomeric forms

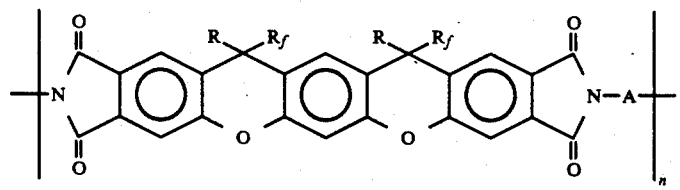

wherein R is selected from the group consisting of aryl, substituted aryl and perfluoroalkyl; $R_f$ is perfluoroalkyl; A is a divalent radical of a diamine containing at least two carbon atoms, the two amino groups of the diamine each being attached to separate carbon atoms of said divalent radical; and n is a positive integer.

23. The polyimide of claim 22, wherein R is $CF_3$ and $R_f$ is $CF_3$.

24. The polyimide of claim 22, wherein R is aryl and $R_f$ is $CF_3$.

* * * * *